United States Patent [19]

Schneider et al.

[11] Patent Number: 5,386,029

[45] Date of Patent: Jan. 31, 1995

[54] PROCESS FOR THE MANUFACTURE OF 4-ACYLOXY-3-HYDROXYETHYL-AZETIDI-NONES

[75] Inventors: Peter Schneider, Bottmingen; Gerardo Ramos, Arlesheim, both of Switzerland

[73] Assignee: Ciba-Geigy Corporation, Ardsley, N.Y.

[21] Appl. No.: 92,736

[22] Filed: Jul. 16, 1993

Related U.S. Application Data

[62] Division of Ser. No. 740,685, Aug. 6, 1991, Pat. No. 5,274,188, which is a division of Ser. No. 491,145, Mar. 9, 1990, Pat. No. 5,064,761, which is a division of Ser. No. 186,547, Apr. 27, 1988, Pat. No. 4,927,507.

Foreign Application Priority Data

May 4, 1987 [CH] Switzerland ............... 1683/87

[51] Int. Cl.$^6$ ............... C07D 265/06; C07D 265/08
[52] U.S. Cl. ............... 544/88; 540/200; 540/357
[58] Field of Search ............... 544/88

*Primary Examiner*—Mukund J. Shah
*Assistant Examiner*—Matthew V. Grumbling
*Attorney, Agent, or Firm*—Irving M. Fishman; Karen G. Kaiser

[57] ABSTRACT

The invention relates to a novel process for the manufacture of (3R,1'R)-4-acyloxy-3-(1'-hydroxyethyl)-2-azetidinones of formula

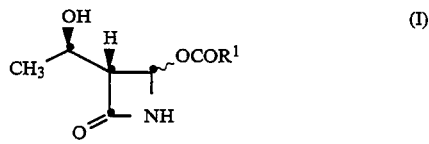

(I)

in which $R^1$ represents lower alkyl or aryl, by enantioselective reduction of the carbonyl group in a suitable α-acylaminomethyl-acetoacetic acid ester, cyclization of the resulting α-acylaminomethyl-β-hydroxybutyric acid ester to a 5,6-dihydro-1,3,4H-oxazine with inversion of the carbon atom carrying the hydroxy group, equilibration to form the preferred trans-substituted dihydrooxazine, recleaving to form the configuratively uniform α-aminomethyl-β-hydroxybutyric acid, ring-closure to form the β-lactam and oxidative acylation at C(4) of the β-lactam. Compounds of formula I can be used as starting materials for the manufacture of β-lactam antibiotics. The invention relates also to novel intermediates.

8 Claims, No Drawings

PROCESS FOR THE MANUFACTURE OF 4-ACYLOXY-3-HYDROXYETHYL-AZETIDINONES

This is a divisional of Ser. No. 07/740,685, filed Aug. 6, 1991 U.S. Pat. No. 5,274,188 which is a divisional of Ser. No. 07/491,145, filed Mar. 9, 1990 now U.S. Pat. No. 5,064,761, which is a divisional of Ser. No. 07/186,547, filed Apr. 27, 1988 now U.S. Pat. No. 4,927,507.

The invention relates to a novel process for the manufacture of 4-acyloxy-3-hydroxyethyl-azetidinones which can be used as starting materials for the manufacture of β-lactam antibiotics. The invention relates also to novel intermediates.

A (3R,1′R)-4-acyloxy-3-(1′-hydroxyethyl)-2-azetidinone of formula I that can be manufactured in accordance with the process of the invention, especially (3R,4R,1′R)-4-acetoxy-3-(1′-hydroxyethyl)-2-azetidinone of formula Ia

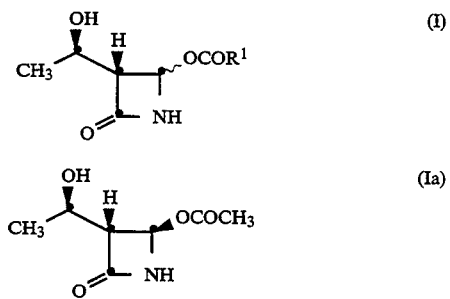

is suitable as a starting material for the manufacture of a large number of highly active β-lactam antibiotics, for example penems, carbapenems or corresponding oxapenem, penicillin or cephalosporin derivatives. In these reactions the acyloxy group in the 4-position of the azetidinone is exchanged for suitable sulphur or carbon nucleophiles. Such reactions are explained in the synoptical article by W. Dürckheimer et al., Angew. Chem. Int. Ed. Engl. 24, 180 (1985).

Penems are obtained, for example, by reacting a compound of formula I, optionally after the introduction of a protecting group at the hydroxy group and/or the lactam nitrogen atom, with a mercaptan, a thio acid, a dithio acid, a trithiocarbonate or a related compound, alkylating or acylating the nitrogen atom with a suitable acetic acid derivative, and finally closing the sulphur-containing five-membered ring. For the synthesis of carbapenems, for example a compound of formula I or a protected derivative of such a compound is reacted with a suitably substituted enol silyl ether, tin enolate, boron enolate, tetraallyltin or a related compound and the resulting products are further processed accordingly.

Essential criteria for the antibiotic activity of penems and carbapenems are not only the nature and the position, but also the spatial configuration, of the substituents. The diastereoisomer of formula Ia has a spatial configuration of the hydroxy, hydroxyethyl and acetoxy groups favouring its use as a starting material for antibiotically active β-lactam antibiotics, but other diastereoisomers are also suitable for further processing: in a substitution reaction with sulphur and carbon nucleophiles under suitable reaction conditions the C(4)-epimeric cis compound (4S) likewise yields the trans-configuration of the substituents at the azetidinone ring, which configuration is already present in the compound of formula Ia.

The manufacture of compounds of formula I is known. For example, EP 78026 and Tetrahedron Letters 23, 2293-2296 (1982) describe a process in which the compound of formula Ia is prepared from L-aspartic acid by the acylation or hydroxyalkylation of the dianion of a N-protected azetidinone-4-carboxylic acid and subsequent oxidative decarboxylation. EP 106652 describes a process in which a Schiff's base of glyoxylic acid is reacted with diketene, the acetyl group in the side chain is reduced to hydroxyethyl, and the enantiomers are separated by way of diastereoisomeric esters. EP 171064 describes a process in which a 4-ethynylazetidinone is synthesised by cycloaddition and the ethynyl radical is then converted into acetyl and finally, by Baeyer-Villiger reaction, into acetoxy. EP 181831 describes a process in which an α,β-epoxybutyrylacetonylamide is cyclised with a base and the resulting 4-acetyl-3-hydroxyethyl-azetidinone is oxidised to the 4-acetoxy compound.

Description of the Process

The invention relates to a process for the manufacture of compounds of formula

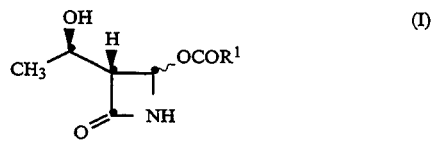

in which $R^1$ represents lower alkyl or aryl, characterised in that a compound of formula

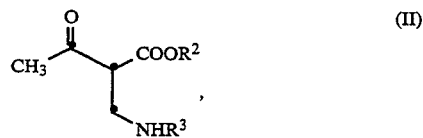

in which $R^2$ represents hydrogen or an esterifying radical and $R^3$ represents hydrogen or the acyl radical of a carboxylic acid or of a carbonic acid semiester, or a salt thereof, is reduced with an enantioselective reducing agent, a resulting compound of formula

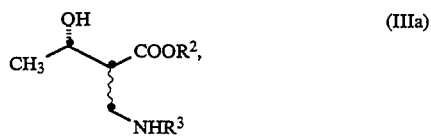

in the case when $R^2$ and/or $R^3$ represent(s) hydrogen, is in any sequence esterified or acylated with a reagent that introduces the acyl radical of a carboxylic acid or of a carbonic acid semiester, and the resulting compound, or the compound of formula IIIa in which $R^2$ already represents an esterifying radical and $R^3$ already represents the acyl radical of a carboxylic acid or of a carbonic acid semiester, or a salt thereof, is cyclised with an agent that activates the hydroxy group, a resulting compound of formula

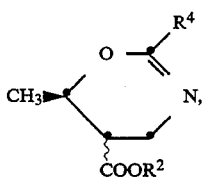

(IV)

in which $R^2$ represents an esterifying radical and $R^4$ represents the radical of a carboxylic acid or of a carbonic acid semiester $R^4COOH$, is isomerised with a base, and a resulting diastereoisomer of formula

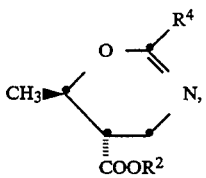

(IVa)

is hydrolysed, the resulting compound of formula

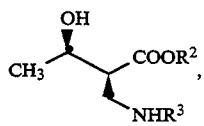

(IIIB)

in which $R^2$ and $R^3$ represent hydrogen, or a salt thereof, is cyclised with an agent removing the elements of water, and the resulting compound of formula

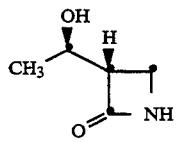

(V)

is oxidised with an agent that introduces the radical $R^1COO-$.

Compared with the processes known hitherto the novel process according to the invention has considerable advantages: it can be used for the manufacture of the compounds of formula I and their diastereoisomers in a high total yield, with high stereoselectivity, few reaction steps and with simple, inexpensive reagents. Surprisingly it is possible, starting from readily available, inexpensive compounds of formula II, to obtain enantiomerically pure diastereoisomers of formula I having three chiral carbon atoms using one enantioselective reduction step and simple subsequent reactions. It is also surprising that the reaction sequence for the manufacture of compound I, which contains a sensitive β-lactam ring, does not require protecting groups.

The general terms and names used in the definition of substituents have preferably the following meanings:

"Lower", for example in lower alkyl, lower alkoxy or lower alkanoyl, means that the radicals and groups so designated, unless otherwise indicated, contain from 1 to 7 carbon atoms and preferably from 1 to 4 carbon atoms.

An esterifying radical $R^2$ is, for example, lower alkyl, cycloalkyl or aryl-lower alkyl, preferably lower alkyl.

The acyl radical $R^3$ of a carboxylic acid or of a carbonic acid semiester is, for example, lower alkanoyl, cycloalkylcarbonyl or arylcarbonyl, or lower alkoxycarbonyl, aryloxycarbonyl or aryl-lower alkoxycarbonyl, respectively. The radical $R^4$ of a carboxylic acid or of a carbonic acid semiester $R^4COOH$ has the corresponding meanings and is therefore, for example, lower alkyl, cycloalkyl or aryl, or lower alkoxy, aryloxy or aryl-lower alkoxy, respectively. The acyl radical $R^3$ is preferably lower alkanoyl or arylcarbonyl and the radical $R^4$ is accordingly lower alkyl or aryl, respectively.

Lower alkyl $R^1$, $R^2$ or $R^4$ has preferably from 1 to 7 carbon atoms and is, for example, methyl, ethyl, n-propyl, isopropyl, n-butyl or tert.-butyl.

Aryl $R^1$ or $R^4$ has from 6 to 14, preferably from 6 to 10, carbon atoms and is, for example, unsubstituted or substituted phenyl, 1-naphthyl or 2-naphthyl. Suitable substituents are, for example, lower alkyl, for example methyl, hydroxy, lower alkoxy, for example methoxy, lower alkanoyloxy, for example acetoxy, halogen, for example chlorine or bromine, or nitro. The substituents, of which there may be one or more, may be in the 2-, 3- or 4-position of the phenyl ring, for example as in 4-methylphenyl, 3,5-dimethylphenyl, 4-methoxyphenyl, 4-chlorophenyl, 4-nitrophenyl, 2,4-dinitrophenyl or 3,5-dinitrophenyl.

Cycloalkyl $R^2$ or $R^4$ contains, for example, from 3 to 8, preferably from 3 to 6, carbon atoms and is, for example, cyclopropyl, cyclopentyl or cyclohexyl.

In aryl-lower alkyl $R^2$, lower alkyl has preferably from 1 to 4 carbon atoms and is, for example, methyl or ethyl. Aryl in aryl-lower alkyl $R^2$ has preferably the meanings given under aryl $R^1$, it also being possible for there to be more than one aryl group, for example two or three. Examples of aryl-lower alkyl $R^2$ are benzyl, 4-methylbenzyl, 4-methoxybenzyl, 4-nitrobenzyl, 2-phenylethyl, diphenylmethyl, di-(4-methoxyphenyl)-methyl, trityl, 1-naphthylmethyl and 2-naphthylmethyl.

Lower alkanoyl $R^3$ has from 1 to 8, preferably from 2 to 5, carbon atoms and is, for example, acetyl, propionyl, butyryl or pivaloyl.

Cycloalkylcarbonyl $R^3$ contains, for example, from 4 to 9, preferably from 4 to 7, carbon atoms and is, for example, cyclopropylcarbonyl, cyclopentylcarbonyl or cyclohexylcarbonyl.

In arylcarbonyl $R^3$, aryl has from 6 to 14 carbon atoms and preferably has the meanings given under aryl $R^1$. Arylcarbonyl $R^3$ is, for example, benzoyl, p-toluyl, 4-methoxybenzoyl, 3,5-dinitrobenzoyl, 1-naphthylcarbonyl or 2-naphthylcarbonyl.

In lower alkoxycarbonyl $R^3$, lower alkoxy has preferably from 1 to 7 carbon atoms and is, for example, methoxy, ethoxy, n-propoxy, n-butoxy or isobutoxy.

In aryloxycarbonyl $R^3$, aryloxy has from 6 to 14, preferably from 6 to 10, carbon atoms and is, for example, unsubstituted or substituted phenoxy, 1-naphthoxy or 2-naphthoxy. Suitable substituents of phenoxy are the radicals mentioned above under aryl $R^1$, for example lower alkyl, for example methyl, lower alkoxy, for example methoxy, halogen, for example chlorine, or nitro.

In aryl-lower alkoxycarbonyl $R^3$, aryl-lower alkoxy consists of lower alkoxy having preferably from 1 to 4 carbon atoms, for example of methoxy or ethoxy, and aryl having the meanings given above under aryl $R^1$, it also being possible for there to be more than one aryl group, for example two or three. Examples of such aryl-lower alkoxy are benzyloxy, 4-methylbenzyloxy, 4-methoxybenzyloxy, 4-nitrobenzyloxy, 2-phenylethoxy and diphenylmethoxy.

Lower alkoxy, aryloxy and aryl-lower alkoxy R$^4$ have, for example, the meanings given above under the corresponding lower alkoxycarbonyl, aryloxycarbonyl and aryl-lower alkoxycarbonyl radicals R$^3$.

Salts are, for example, acid addition salts of the amine group in compounds of formula II, III, IIIa or IIIb, for example with inorganic acids, for example hydrochloric acid, sulphuric acid, nitric acid or phosphoric acid, or with organic carboxylic or sulphonic acids, for example acetic acid, chloroacetic acid, trichloroacetic acid, trifluoroacetic acid, propionic acid, glycolic acid, fumaric acid, benzoic acid, methanesulphonic acid, trifluoromethanesulphonic acid, ethanesulphonic acid, camphor-10-sulphonic acid, benzenesulphonic acid, toluenesulphonic acid, 4-nitrobenzenesulphonic acid, 2,4-dinitrobenzenesulphonic acid or naphthalene-2-sulphonic acid. Other acid addition salts are formed from the nitrogen of the imide ester group in 1,3-oxazines of formula IV or IVa with strong acids, for example mineral acids, for example hydrochloric acid or sulphuric acid, or with organic sulphonic acids, for example the sulphonic acids mentioned above.

Carboxylic acids of formula II, III, IIIa or IIIb can form alkali metal salts, for example sodium or potassium salts, and also alkaline earth metal salts, for example magnesium or calcium salts, heavy metal salts, for example copper, lead or zinc salts, ammonium salts, salts with organic amines, for example with optionally substituted mono-, di- or tri-alkylamines, for example cyclohexylamine, diethylamine, cyclohexylethylamine, dibutylamine, trimethylamine, triethylamine or tri-(2-hydroxyethyl)-amine, or with tetra-substituted organic ammonium ions, for example tetramethylammonium, tetraethylammonium or tetrabutylammonium.

Compounds of formulae II, III, IIIa and IIIb in which R$^2$ and R$^3$ represent hydrogen can also form internal salts.

A compound of formula I or Ia has three chiral carbon atoms that are independent of one another, namely carbon atoms 3 and 4 of the β-lactam ring and carbon atom 1' carrying the hydroxy group of the hydroxyethyl side chain. The formula I includes two diastereoisomeric compounds, namely the (3R,4R,1'R)-isomer, for example the compound of formula Ia, and the (3R,4S,1'R)-isomer.

The compounds of formulae III, IIIa, IIIb, IV and IVa have two chiral carbon atoms that are independent of one another. The formula

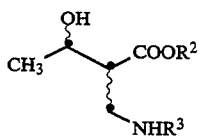

(III)

includes all four possible diastereoisomers. The formula IIIa includes two of these diastereoisomers, namely the (2R,3S)-isomer and the (2S,3S)-isomer. In contrast, a compound of formula IIIb has the (2S,3R)-configuration. The formula IV likewise includes two diastereoisomeric compounds, namely the (5R,6R)-isomer and the (5S,6R)-isomer, that is to say the compound of formula IVa.

The compound of formula V is of uniform configuration and is the (3S,1'R)-isomer.

In the context of this description, "diastereoisomerically pure" indicates that the diastereoisomer so defined is present in an amount of at least 80% in admixture with other diastereoisomers. This high proportion of the one diastereoisomer means that it is possible, by simple physical separating methods, for example by recrystallisation of a compound according to the invention, a suitable salt or a suitable derivative, for the proportion of that diastereoisomer to be increased to, for example, more than 95% or to be increased to such an extent that the other diastereoisomers can no longer be detected using conventional analytical methods. "Enantiomerically pure" has an analogous definition.

Process Steps

The reduction of a compound of formula II is effected by a chemical or biochemical method.

A suitable enantioselective reducing agent is a reducing agent that, when reacted with compounds of formula II, yields predominantly diastereoisomers of formula IIIa having the (3S)-configuration, i.e. produces an optically active compound from a racemic starting material. As regards the process according to the invention it is immaterial whether at the same time also a configuration at C(2), for example the (2S)-configuration, is preferred.

A preferred example of a biochemical enantioselective reducing agent is baker's yeast (*Saccharomyces cerevisiae*) and the oxidoreductases present in baker's yeast. It is possible to use for the reduction baker's yeast of any origin, for example the baker's yeast obtainable from the American Type Culture Collection under the number ATCC 26403. Other yeasts and other fungi are also suitable, for example *Candida albicans, Geotrichum candidum, Schizosaccharomyces pombe, Saccharomyces acidifaciens Rhodotorula rubra, Curvularia lunata, Curvularia falcata* or *Mortierella ramanniana*. Also suitable are isolated oxidoreductases, preferably oxidoreductases dependent on β-nicotinamide adenine dinucleotide dihydride (NADH) or on NADH phosphate (NADPH), for example yeast-alcohol dehydrogenase, dihydroxyacetone reductase obtained from *Mucor javanicus*, β-hydroxyacyl-CoA dehydrogenase obtained from pig's heart, fatty acid synthetase (containing a β-keto-reductase component) obtained from baker's yeast, D-β-hydroxybutyrate dehydrogenase obtained from *Pseudomonas lemoignei* or *Rhodopseudomonas spheroides*, and other oxidoreductases.

In the case of reduction with whole cells, for example with baker's yeast, the microorganism is kept under physiological conditions in a suitable preculture and, if necessary, expanded. The culture media are the customary media, for example buffered glucose solution, which, if desired, may contain trace elements, having a pH value of from 6 to 8. The substrate of formula II is added to the culture medium in concentrations of from 1 to 50 g per liter, and further glucose, which assumes the function of hydrogen donor, or other carbohydrates, and also, for example, a formate, a hypophosphite or ethanol as hydrogen donors, are added. The culture is kept at from room temperature to 40° C., preferably at slightly elevated temperature, for example from 30° C. to 37° C., and is mixed intensively.

In the case of reduction with isolated enzymes, it is preferable to add a further enzyme that regenerates in situ the NADH or NADPH required for the oxidoreductase, for example *Clostridium kluyveri* or enzymes obtained from *C. kluyveri*. Suitable hydrogen donors are molecular hydrogen, a formate, a hypophosphite or an electrochemical reduction in the presence of a viologen, for example methyl viologen. It is also possible to regenerate NADH or NADPH without further enzymes using, for example, ethanol or formate.

Chemical enantioselective reducing agents are, for example, hydrogen in the presence of a chiral heterogeneous catalyst or a chiral homogeneous catalyst, or chiral boranes and borohydrides and chiral aluminium hydrides.

A chiral heterogeneous catalyst is, for example, a Raney nickel catalyst modified with enantiomerically pure tartaric acid and sodium bromide, or a platinum catalyst modified with a chiral amine, for example enantiomerically pure 1-phenylethylamine. Suitable chiral homogeneous catalysts are, for example, rhodium bisphosphine hydride complexes in which the phosphine is chiral, for example containing enantiomerically pure cyclohexyl-methyl-o-methoxyphenyl-phosphine or 2,3-O-isopropylidene-2,3-di-hydroxy-1,4-bis-(diphenylphosphino)-butane (DIOP).

Suitable chiral boranes and borohydrides are, for example, enantiomerically pure diisopinocampheylborane or lithium-$\beta$-isopinocampheyl-9-borabicyclo[3.3.1]nonyl hydride. Suitable chiral aluminium hydrides are obtained by reaction of lithium aluminium hydride with equivalent amounts of an enantiomerically pure, chiral alcohol, amine or aminoalcohol, for example 1,1'-di($\beta$-naphthol), o,o-dimethyl-N-pyrrolidinylmethyl-aniline or darvon alcohol.

The mentioned chemical enantioselective reducing agents are used under the customary reaction conditions. Hydrogenations in the presence of chiral heterogeneous or homogeneous catalysts are carried out, for example, depending upon the nature of the catalyst, at a hydrogen pressure of from 1 to 100 bar and at temperatures of from 0° to 120° C. in an inert solvent, for example in an alcohol, for example ethanol, an ester, for example ethyl acetate, or a hydrocarbon, for example cyclohexane or toluene. For the reduction with chiral boranes, borohydrides and aluminium hydrides there are preferably used anhydrous ethereal solvents, for example diethyl ether, tetrahydrofuran or 1,2-dimethoxyethane, and temperatures of from −80° to +50° C., preferably from −30° to 0° C.

If, in a compound of formula IIIa obtainable by enantioselective reduction, $R^2$ represents hydrogen, then the free carboxy group must be esterified before the ring-closure to form a compound of formula IV. The esterification is carried out under the customary conditions, for example by reaction with an excess of the corresponding alcohol $R^2OH$, for example a lower alkanol, cycloalkanol or aryl-lower alkanol, in the presence of an acid, for example a mineral acid which is as far as possible anhydrous, for example hydrogen chloride, concentrated sulphuric acid, polyphosphoric acid or phosphorus pentoxide, an organic sulphonic acid, for example p-toluenesulphonic acid, an acidic ion exchanger or a Lewis acid, for example boron trifluoride etherate, if desired in the presence of an agent removing the elements of water, for example a molecular sieve, or with removal of the water of reaction by azeotropic distillation, for example with a halogenated hydrocarbon, for example methylene chloride, chloroform or carbon tetrachloride, or an aromatic hydrocarbon, for example benzene or toluene. The acidic esterification is carried out, for example, at temperatures of from 0° to the boiling point of the alcohol $R^2OH$ or of the azeotrope with the mentioned entraining solvents. Esterification can also be achieved using an alkylating agent, for example using diazomethane in ethereal solution or using benzyl chloride and the sodium or, preferably, caesium salt of the compound of formula IIIa.

If, in a compound of formula IIIa obtainable by enantioselective reduction, $R^3$ represents hydrogen, then the free amino group must be acylated before the ring-closure to form a compound of formula IV. The acylation is effected under the customary reaction conditions, for example using the carboxylic acid anhydride or carboxylic acid halide, for example carboxylic acid chloride, corresponding to the acyl group $R^3$ or using the carbonic acid semiester derivative, for example haloformic acid ester, for example chloroformic acid ester, corresponding to the acyl group $R^3$, optionally with the addition of an acid, for example p-toluenesulphonic acid, or a base, for example a tertiary amine, for example triethylamine, dimethylbenzylamine or N-methylmorpholine, an amidine, for example 1,5-diazabicyclo[4.3.0]non-5-ene or 1,8-diazabicyclo[5.4.0]undec-7-ene, a pyridine base, for example pyridine, lutidine or 4-dimethylaminopyridine, or an alkali metal or alkaline earth metal carbonate, for example sodium, potassium or calcium carbonate, in an inert solvent, for example in an ether, for example diethyl ether, tetrahydrofuran or dioxan, a halogenated hydrocarbon, for example methylene chloride, an ester, for example ethyl acetate, an amide, for example dimethylformamide or N-methylpyrrolidone, or in a nitrile, for example acetonitrile, at temperatures of from −20° C. to the boiling point of the solvent, preferably from 0° to 50° C. An excess of the acylating agent should be avoided in order that the hydroxy group of the compound of formula IIIa is not acylated at the same time.

The sequence for the mentioned esterification and acylation steps may be freely selected.

A compound of formula IIIa in which $R^2$ is an esterifying radical, for example lower alkyl, cycloalkyl or aryl-lower alkyl, and $R^3$ is the acyl radical of a carboxylic acid or of a carbonic acid semiester, for example lower alkanoyl, cycloalkylcarbonyl or arylcarbonyl, or lower alkoxycarbonyl, aryloxycarbonyl or aryl-lower alkoxycarbonyl, respectively, is cyclised with an agent that activates the hydroxy group at C(3) to form a 5,6-dihydro-1,3,4H-oxazine of formula IV. The hydroxy group is converted into a nucleofugal leaving group and is intramolecularly substituted, with inversion, by the oxygen of the carbonyl group of the radical $R^3$.

Suitable agents activating the hydroxy group are, for example, the halogenating agents customarily used for the manufacture of halides from alcohols, for example phosphorus halides, for example phosphorus pentachloride, phosphorus trichloride, phosphorus tribromide, triphenylphosphine dichloride, triphenylphosphine dibromide or equivalent amounts of triphenylphosphine and carbon tetrachloride, and also reactive organic acid halides, for example phosgene, oxalyl chloride, cyanuric chloride or dimethylformamidinium chloride, or especially thionyl chloride. Using these halogenating agents the hydroxy group at C(3) is converted into an activated inorganic or organic ester which does not, however, then react with a halide ion in customary manner, but is substituted intramolecularly by the oxygen of the carbonyl group. The reaction is carried out without solvents or, preferably, in an inert solvent, for example in a hydrocarbon, for example toluene, a chlorinated hydrocarbon, for example methylene chloride, an ester, for example ethyl acetate, or an ether, for example diethyl ether or dioxan, at temperatures of from 0° to 150° C., for example at the boiling point of the solvent or at room temperature. If desired, it is possible to add a base which binds the hydrogen halide that is freed, for example a tertiary amine, for example triethylamine, dimethylaniline or N-methylmorpholine, or a pyridine base, for example pyridine, and also, if desired, catalytic amounts of an amide, for example dimethylformamide or hexamethylphosphoric acid triamide, or a Lewis acid, for example zinc chloride or aluminium chloride. The reaction is preferably carried out with equivalent amounts or with a slight excess, for example from 1.05 to 1.5 equivalents, of the halogenating agent.

Other suitable agents activating the hydroxy group are reagents for the manufacture of sulphonates from alcohols, for example sulphonic acid halides, for example methanesulphonic acid chloride, benzenesulphonic acid chloride, p-toluenesulphonic acid chloride, p-nitrobenzenesulphonic acid chloride or 2,4-dinitrobenzenesulphonic acid chloride, or sulphonic acid anhydrides, for example trifluoromethanesulphonic acid anhydride. These reagents are used, for example, in the inert solvents mentioned above for the halogenating agents, for example methylene chloride or diethyl ether, in the presence of one of the mentioned bases, for example triethylamine, at temperatures of from −30° to 50° C., for example from 0° C. to room temperature.

Further agents activating the hydroxy group are reactive carbonyl derivatives, for example carbonylbisimidazole or di-2-pyridylcarbonate, and combinations of azo compounds with phosphines, for example azodicarboxylic acid diethyl ester and triphenylphosphine or 4-methyl-1,2,4-triazolidine-3,5-dione and triphenylphosphine. The mentioned reagents are preferably used in polar inert solvents, for example acetonitrile, tetrahydrofuran or 1,2-dimethoxyethane, at temperatures of from −30° to +50° C., for example from 0° C. to room temperature.

In a compound of formula IV in which $R^2$ is an esterifying radical, for example lower alkyl, cycloalkyl or aryl-lower alkyl, and $R^4$ is the radical of a carboxylic acid or of a carbonic acid semiester $R^4COOH$, for example lower alkyl, cycloalkyl or aryl, or lower alkoxy, aryloxy or aryl-lower alkoxy, respectively, it is possible by treatment with suitable bases to effect the conversion of the (5R,6R)-diastereoisomer, or of mixtures of the (5R,6R)- and (5S,6R)-diastereoisomers, into the diastereoisomerically pure compound of formula IVa having the (5S,6R)-configuration, that is to say the trans-configuration of the substituents $CH_3$ and $COOR^2$ at the six-membered ring. Suitable bases for such an isomerisation are, for example, tertiary amines, for example triethylamine or tributylamine, pyridine or pyridine derivatives, for example lutidine, amidine bases, for example 1,5-diazabicyclo[4.3.0]non-5-ene or 1,8-diazabicyclo[5.4.0]undec-7-ene, alkali metal salts of sterically hindered, secondary amines, for example lithium diisopropylamide or lithium hexamethyldisilazide, or basic alkali metal and alkaline earth metal salts, for example sodium or potassium carbonate or potassium fluoride. The isomerisation is carried out, for example, in polar, anhydrous solvents, for example ethanol, tert.-butanol, tetrahydrofuran, dioxan or acetonitrile, at temperatures of from 50° to 100° C., or in nonpolar, anhydrous solvents, for example aromatic hydrocarbons, for example toluene, chlorobenzene or dichlorobenzene, at temperatures of from 80° to 150° C., for example at the boiling point of the solvent.

In the next step, in a compound of formula IVa the 1,3-oxazine ring is cleaved and at the same time the acylamino group and the ester function are hydrolysed. The hydrolysis is preferably carried out with acids, but is also possible with bases.

Suitable acids are, for example, mineral acids, for example hydrochloric acid, sulphuric acid or phosphoric acid, or strong organic acids, for example alkane- or arene-sulphonic acids, for example methanesulphonic acid, trifluoromethanesulphonic acid, benzenesulphonic acid, p-toluenesulphonic acid or p-nitrobenzenesulphonic acid, preferably in aqueous solution, for example in water or in mixtures of water and organic solvents, for example ethanol, dioxan, ethylene glycol monomethyl ether or monobutyl ether, at temperatures of from 80° to 150° C., preferably at about 100° C.

Suitable bases are metal hydroxides, for example alkali metal hydroxides, for example lithium, sodium or potassium hydroxide, alkali metal carbonates, for example sodium or potassium carbonate, or tetra-substituted ammonium hydroxides, for example benzyltrimethylammonium hydroxide, preferably in water or the above-mentioned mixtures of water and organic solvents, at temperatures of from 50° to 120° C., for example at about 80° C. The basic hydrolysis can be accelerated by the addition of hydrogen peroxide, for example in the form of a 30% aqueous solution.

The compound of formula IIIb in which $R^2$ and $R^3$ represent hydrogen obtainable in the hydrolysis is cyclised using the customary agents removing the elements of water to form the $\beta$-lactam of formula V. Suitable agents removing the elements of water are acetyl chloride, thionyl chloride or phosphorus trichloride, acetic anhydride, triethylaluminium, triisobutylaluminium or the like, but preferably a carbodiimide, for example dicyclohexylcarbodiimide or diisopropylcarbodiimide, 2-chloro-1-methylpyridinium iodide, or 2,2'-dipyridyldisulphide in the presence of a phosphine, for example triphenylphosphine. Carbodiimides are preferably used in the presence of equivalent amounts of a tertiary amine, for example triethylamine, or a pyridine base, for example pyridine, in an inert polar solvent, for example acetonitrile, dimethylformamide, nitromethane, tetrahydrofuran or dioxan, at temperatures of from 25° to 80° C., for example at about 50° C. In the case of the reaction with 2-chloro-1-methylpyridinium iodide, an equivalent amount of a tertiary amine, for example triethylamine, is added and the condensation is effected at temperatures of from 0° to 50° C., for example at about room temperature, in an inert solvent, for example methylene chloride. The condensation with 2,2'-dipyridyldisulphide and triphenylphosphine is carried out in one of the mentioned polar solvents, preferably in acetonitrile, at temperatures of from 50° to 85° C., for example at the boiling point of acetonitrile. Instead of 2,2'-dipyridyldisulphide it is alternatively possible to use catalytic amounts of 2-mercaptopyridine and an equivalent amount of a mild oxidising agent, for example manganese oxide.

Also suitable as agents removing the elements of water are the reagents used in peptide chemistry for the condensation of $\alpha$-amino acids, for example bis-(2-oxo-3-oxazolidinyl)-phosphinic acid chloride, 1-benzotriazolyloxy-tris(dimethylamino)-phosphonium hexafluorophosphate or 2-ethoxy-1-ethoxycarbonyl-1,2-dihydroquinoline.

The compound of formula V is oxidised to form a compound of formula I with an agent that introduces the radical $R^1COO-$. The oxidation is effected chemically or, preferably, electrochemically.

Chemical oxidising agents that introduce the radical $R^1COO-$ are, for example, the corresponding acyl peroxides, for example acetyl-tert.-butyl peroxide, propionyl-tert.-butyl peroxide, benzoyl-tert.-butyl peroxide or dibenzoyl peroxide. Preferably, the tert.-butyl peroxides are reacted with catalytic amounts of a copper(I) salt, for example copper(I) chloride, bromide or 2-ethylhexanoate, in an inert solvent, for example benzene, petroleum ether, acetonitrile or acetonitrile/glacial acetic acid. A catalyst is unnecessary in the case of the reaction with dibenzoyl peroxide. Other oxidising agents that introduce the acetyl radical are, for example, lead tetraacetate and mercury diacetate.

For the electrochemical oxidation, a monocell or a divided cell with a mechanical diaphragm, for example, of porous clay, glass or plastics, for example polyvinyl chloride or polypropylene, or with an ion exchanger diaphragm, for example as available under the trade name Nafion, and with electrodes made of noble metal, for example platinum, titanium alloys, for example titanium/iridium or titanium/tantalum, also nickel, lead dioxide, glass carbon and/or graphite, is used. The electrochemical oxidative acylation is carried out in the carboxylic acid corresponding to the radical $R^1$, for example acetic acid or propionic acid, or in mixtures of this acid and inert organic solvents, for example acetonitrile, dioxan or dimethylformamide, or tertiary amines, for example triethylamine, for example in mixtures of acetic acid/acetonitrile, acetic acid/triethylamine, propionic acid/acetonitrile or benzoic acid/acetonitrile, there being added conducting salts, for example lithium, sodium, potassium or tetraalkylammonium salts, for example lithium, sodium, tetraethylammonium or tetrabutylammonium tetrafluoroborate, acetate or nitrate. Suitable current densities for the electrolysis are from 10 to 400 $mA/cm^2$, for example about 50 $mA/cm^2$, at temperatures of from 0° to 50° C., preferably from room temperature to 30° C.

Both the chemical oxidative acylation and the electrochemical oxidative acylation yield preferentially a compound of formula I in which the hydroxyethyl group at C(3) and the acyloxy group at C(4) are arranged in the trans-configuration relative to one another, that is to say yield the diastereoisomer having the (3R,4R,1'R)configuration.

Salts of the mentioned compounds are obtained in customary manner. Acid addition salts of the amino group in compounds of formula II, III, IIIa or IIIb or of the nitrogen atom of the imide ester group in compounds of formula IV or IVa are formed, for example, by treatment with an acid or a suitable anion exchanger reagent, preferably stoichiometric amounts or only a small excess of the salt-forming agent being used. Internal salts, for example of compounds of formula II, III, IIIa or IIIb, that contain a free carboxy group and a free amino group can be formed, for example, by neutralising salts, such as acid addition salts, to the isoelectric point, for example with bases, or by treatment with ion exchangers or epoxides, for example propylene oxide. Salts of compounds of formula II, III, IIIa or IIIb containing carboxy groups can be formed, for example, by treatment with metal compounds, such as alkali metal salts of suitable organic carboxylic acids, for example the sodium salt of 2-ethylhexanoic acid, with inorganic alkali metal or alkaline earth metal salts, for example sodium hydrogen carbonate, a stoichiometric amount or a small excess of an alkali metal hydroxide, for example lithium, sodium or potassium hydroxide, or with ammonia or a suitable organic amine.

Salts can be converted in customary manner into the free compounds: metal and ammonium salts, for example, by treatment with suitable acids, and acid addition salts, for example, by treatment with a suitable basic agent.

The process of the invention also includes those forms in which intermediates are isolated and the remaining process steps are carried out with them; in which starting materials and reagents are produced in situ and/or intermediates and end products are processed further without being isolated, and also in which a compound of formula II is reduced directly to a diastereoisomerically pure compound of formula IIIb, and ring-closure to form the oxazine of formula IV, isomerisation to form IVa and recleaving to form the diastereoisomerically pure compound of formula IIIb is superfluous.

The invention relates especially also to the novel process steps mentioned hereinbelow under the mentioned preferred reaction conditions as such or as part of a whole process for the manufacture of compounds of formula I.

A preferred process is a process for the manufacture of compounds of formula I in which $R^1$ represents lower alkyl or aryl, characterised in that the compound of formula V is oxidatively acylated electrochemically in the presence of an acid $R^1COOH$ at current densities of from 10 to 400 $mA/cm^2$ and temperatures of from 0° to 50° C. The said process step is more especially preferred for the manufacture of a compound of formula Ia in which $R^1$ represents methyl.

A further preferred process is a process for the manufacture of compounds of formula IIIa in which $R^2$ represents hydrogen or an esterifying radical, for example lower alkyl, cycloalkyl or aryl-lower alkyl, and $R^3$ represents hydrogen or the acyl radical of a carboxylic acid or of a carbonic acid semiester, for example lower alkanoyl, cycloalkylcarbonyl or arylcarbonyl, or lower alkoxycarbonyl, aryloxycarbonyl or aryl-lower alkoxycarbonyl, respectively, characterised in that a compound of formula II in which $R^2$ and $R^3$ have the meanings mentioned, or a salt thereof, is reduced with baker's yeast. The said process step is more especially preferred for the reduction of compounds of formula II in which $R^2$ represents hydrogen or lower alkyl and $R^3$ represents lower alkanoyl or arylcarbonyl.

The invention relates especially to the processes described in the Examples.

Further Processing

The compound of formula I and especially the pure diastereoisomer of formula Ia can be converted according to one of the many processes known in the prior art into valuable end products. Most of these processes require for this purpose a derivative of the compound of formula I in which the hydroxy group and/or the β-lactam nitrogen atom are protected by a protecting group. Such protecting groups can readily be introduced, for example in a manner described in standard works on protecting groups.

Advantageously, however, a compound of formula I is further processed without protecting groups in order to avoid additional reaction steps. For example, the compound of formula Ia can, as described in European Patent Application No. 215 739, be reacted with N- allyloxycarbonyl-thioglycine, which is an α-aminothiocarboxylic acid protected at the nitrogen atom, and can be processed in a few steps to the highly active antibiotic (5R,6S,1′R)-2-aminomethyl-6-(1′-hydroxyethyl)-2-penem-3-carboxylic acid. The valuable properties of the said end product and its use are described, for example, in German Patent Application No. 34 31 980.

Intermediates

The invention relates also to novel intermediates and processes for their manufacture.

The invention relates to compounds of formula III in which $R^2$ represents hydrogen or an esterifying radical, for example lower alkyl, for example methyl or ethyl, cycloalkyl, for example cyclohexyl, or aryl-lower alkyl, for example benzyl, and $R^3$ represents hydrogen or the acyl radical of a carboxylic acid or of a carbonic acid semiester, for example lower alkànoyl, for example acetyl or propionyl, cycloalkylcarbonyl, for example cyclohexylcarbonyl, or arylcarbonyl, for example benzoyl, or lower alkoxycarbonyl, for example ethoxycarbonyl or n-butoxycarbonyl, aryloxycarbonyl, for example phenoxycarbonyl, or aryl-lower alkoxycarbonyl, for example benzyloxycarbonyl, respectively, and pure diastereoisomers, mixtures of two diastereoisomers and salts thereof.

The invention relates especially to compounds of formula III in which $R^2$ represents hydrogen or lower alkyl, for example methyl or ethyl, and $R^3$ represents hydrogen, lower alkanoyl, for example acetyl, or arylcarbonyl, for example benzoyl, their pure diastereoisomers, for example the diastereoisomer of formula IIIb, mixtures of two diastereoisomers, for example of formula IIIa, and salts thereof.

The invention relates more especially to compounds of formula IIIa in which $R^2$ represents hydrogen or lower alkyl, for example methyl or ethyl, and $R^3$ represents lower alkanoyl, for example acetyl, or arylcarbonyl, for example benzoyl, their pure diastereoisomers, and salts thereof, and also to the compound of formula IIIb in which $R^2$ and $R^3$ represent hydrogen, and salts thereof.

The invention relates also to compounds of formula IV in which $R^2$ represents an esterifying radical, for example lower alkyl, for example methyl or ethyl, cycloalkyl, for example cyclohexyl, or aryl-lower alkyl, for example benzyl, and $R^4$ represents the radical of a carboxylic acid or of a carbonic acid semiester $R^4COOH$, for example lower alkyl, for example methyl or ethyl, cycloalkyl, for example cyclohexyl, or aryl, for example phenyl, or lower alkoxy, for example ethoxy or n-butoxy, aryloxy, for example phenoxy, or aryl-lower alkoxy, for example benzyloxy, respectively, their pure diastereoisomers, and salts thereof.

The invention relates especially to compounds of formula IV in which $R^2$ represents lower alkyl, for example methyl or ethyl, and $R^4$ represents lower alkyl, for example methyl, or aryl, for example phenyl, their pure diastereoisomers, for example the diastereoisomer of formula IVa, and salts thereof.

The invention relates also to the compound of formula V.

The invention relates especially to the intermediates mentioned in the Examples.

Processes for the manufacture of the mentioned intermediates are especially the corresponding process steps of the whole process according to the invention described above. The processes also include aftertreatments known per se, for example the conversion of compounds according to the invention into other compounds according to the invention and the conversion of free compounds into their salts or of salts into the corresponding free compounds or into different salts.

Starting materials of formula II are known or can be manufactured according to known methods, for example by amidoalkylation of acetoacetic acid esters with acylamido-chloromethane according to H. Böhme et al., Chemische Berichte 92, 1599 (1959).

The following Examples serve to illustrate the invention but do not limit the scope thereof in any way.

EXAMPLE 1

Reduction of α-benzoylaminomethyl-acetoacetic acid ethyl ester with baker's yeast 200 ml of phosphate buffer (pH 7.0), 30 g of baker's yeast (manufactured by Klipfel) and 40 g of glucose are shaken in a 500 ml Erlenmeyer flask at 33° C. and 250 rpm. After 30 minutes, 20.7 g of α-benzoylaminomethylacetoacetic acid ethyl ester are added, then after 24 hours a further 25 g of glucose and, after 48 hours, a further 15 g of glucose are added. The mixture is shaken for a total of 144 hours at 33° C. The reaction solution is filtered over Celite ™, the aqueous solution is extracted seven times with ethyl acetate, and the organic phase is dried over sodium sulphate and the solvent is removed in a rotary evaporator. The residue is separated by chromatography on silica gel with toluene and ethyl acetate:

(2S,3S)-2-benzoylaminomethyl-3-hydroxybutyric acid ethyl ester; m.p. 72°–73° C.; $[\alpha]_D = -30.2°$ (dioxan, c=0.14%); UV (ethanol) $\lambda_{max}=226$ nm ($\epsilon=11540$); IR ($CH_2Cl_2$) 3449, 1721, 1663, 1579 cm $^{-1}$; TLC (silica gel, toluene/ethyl acetate 1:2) $R_f=0.32$.

(2R,3S)-2-benzoylaminomethyl-3-hydroxybutyric acid ethyl ester; oil; $[\alpha]_D = -9.1°$ (dioxan, c=0.14%); UV (ethanol) $\lambda_{max}=226$ nm ($\epsilon=11000$); IR ($CH_2Cl_2$) 3444, 1719, 1647, 1601, 1578 cm $^{-1}$; TLC (silica gel, toluene/ethyl acetate 1:2) $R_f=0.38$.

The enantiomeric purity of the (2S,3S)- and (2R,3S)-esters is checked after derivatisation with the Mosher reagent R(+)-α-methoxy-α-trifluoromethyl-phenylacetic acid chloride using proton nuclear resonance spectroscopy and HPLC (high performance liquid chromatography) and is more than 99%.

The aqueous phase is adjusted to pH 2 with 4N HCl and the acids are extracted with seven 250 ml portions of ethyl acetate. The combined organic phases are dried over sodium sulphate and concentrated by evaporation. The residue is separated by reverse phase chromatography on Opti $UPC_{12}$® silica gel with water:

(2S,3S)-2-benzoylaminomethyl-3-hydroxybutyric acid; m.p. 99°–101° C. (from ethyl acetate); $[\alpha]_D = -21.2°$ (dioxan, c=0.55%); UV (ethanol) $\lambda_{max}=227$ nm ($\epsilon=11360$); IR ($CH_2Cl_2$) 3312, 1735, 1577, 1490 cm$^{-1}$; TLC ($UPC_{12}$, water/acetonitrile 9:1) $R_f=0.25$.

(2R,3S)-2-benzoylaminomethyl-3-hydroxybutyric acid; isolated as the cyclohexylammonium salt; $[\alpha]_D = +10°$ (ethanol, c=0.72%); UV (ethanol) $\lambda_{max}=227$ nm ($\epsilon=11000$); IR ($CH_2Cl_2$) 3381, 1657 , 1625, 1518 , 1486 cm$^{-1}$; TLC ($UPC_{12}$, water/acetonitrile 9:1) $R_f=0.33$.

The acids are esterified as follows: 620 mg of a mixture of the acids are heated at 45° C. for 28 hours in 12 ml of ethanol containing 250 mg of p-toluenesulphonic acid. The reaction solution is concentrated, diluted with ethyl acetate, washed with saturated sodium hydrogen carbonate solution, dried and concentrated by evaporation. The ethyl esters formed are identical to the esters mentioned above, $R_f$ (silica gel, toluene/ethyl acetate 1:2)=0.32 and 0.38, enantiomeric purity more than 99%.

EXAMPLE 2

Reduction of α-benzoylaminomethyl-acetoacetic acid ethyl ester with hydrogen, platinum and a chiral amine 40 mg of platinum oxide and 0.28 ml of R(+)-1-phenylethylamine are prehydrogenated in 20 ml of toluene at normal pressure for 1 hour. 4 g of α-benzoylaminomethyl-acetoacetic acid ethyl ester in 20 ml of toluene are then added and the mixture is hydrogenated at normal pressure and room temperature for 22 hours. The reaction solution is filtered and concentrated by evaporation. The isomeric composition of the resulting 2-benzoylaminomethyl-3-hydroxybutyric acid ethyl ester is determined by gas chromatography on a chiral stationary phase (Chirasil-Val®) and is (2S,3R):(2R,3S):(2S,3S):(2R,3R)=13:14:24:49.

If the enantiomeric S(−)-1-phenylethylamine is used instead of R(+)-1-phenylethylamine, then an isomeric ratio of (2S,3R):(2R,3S):(2S,3S/2R,3R)=10:21:69 is obtained.

EXAMPLE 3

Reduction of α-acetylaminomethyl-acetoacetic acid ethyl ester with hydrogen, platinum and a chiral amine In a manner analogous to Example 2, 4.1 g of α-acetylaminomethyl-acetoacetic acid ethyl ester in toluene are hydrogenated over 41 mg of platinum oxide in the presence of 0.38 ml of S(−)-1-phenylethylamine and worked up. Gas chromatographic analysis on Chirasil-Val® gives an isomeric ratio of (2S,3R):(2R,3S):(2S,3S):(2R,3R)=20:19:22:39.

Using R(+)-1-phenylethylamine, an isomeric ratio of (2S,3R):(2R,3S):(2S,3S):(2R,3R)=16:22:22:39 is obtained.

EXAMPLE 4

(5S,6R)-6-methyl-2-phenyl-5,6-dihydro-1,3,4H-oxazinyl-5-carboxylic acid ethyl ester 0.123 ml of thionyl chloride is added to a solution of 300 mg of (2S,3S)-2-benzoylaminomethyl-3-hydroxybutyric acid ethyl ester in 0.6 ml of methylene chloride and stirred at room temperature for 3 hours. The reaction solution is concentrated on a rotary evaporator, taken up in toluene and concentrated by evaporation. The residue is suspended in a small amount of ethyl acetate and the hydrochloride of the title compound, obtained in crystalline form and having a melting point of 125°–126° C., is filtered off. $[\alpha]_D$=+25.6° (water, c=0.09%); UV (ethanol) $\lambda_{max}$=236 nm (ε=11000); IR (CH$_2$Cl$_2$) 1737, 1656, 1379 cm$^{-1}$.

The hydrochloride is taken up in ethyl acetate and washed with saturated sodium hydrogen carbonate solution. The organic phase is dried with sodium sulphate and the free base is isolated in the form of an oil. TLC (silica gel, toluene/ethyl acetate 1:1) $R_f$=0.69; $[\alpha]_D$=+81.4° (dioxan, c=0.30%); UV (ethanol) $\lambda_{max}$=235 nm (ε=13930); IR (CH$_2$Cl$_2$) 1727, 1659 cm$^{-1}$.

EXAMPLE 5

(5R,6R)-6-methyl-2-phenyl-5,6-dihydro-1,3,4H-oxazinyl-5-carboxylic acid ethyl ester In a manner analogous to Example 4, 1.6 g of (2R,3S)-2-benzoylaminomethyl-3-hydroxybutyric acid ethyl ester are cyclised with 0.66 ml of thionyl chloride in methylene chloride. The title compound is isolated in the form of an oil. TLC (silica gel, toluene/ethyl acetate 1:1) $R_f$=0.55; $[\alpha]_D$=−9.6° (dioxan, c=0.31%); UV (ethanol) $\lambda_{max}$=234 nm (ε=12120); IR (CH$_2$Cl$_2$) 1730, 1658 cm$^{-1}$.

EXAMPLE 6

Isomerisation of 6-methyl-2-phenyl-5,6-dihydro-1,3,4H-oxazinyl-5-carboxylic acid ethyl ester 247 mg of the (5R,6R)-isomer of the title compound are dissolved in 1 ml of dioxan, and 0.05 ml of 1,8-diazabicyclo[5.4.0]undec-7-ene is added. The mixture is heated at 90° C. for 7 hours, then diluted with toluene and washed twice with dilute sodium chloride solution. The organic phase is dried with sodium sulphate and concentrated, and the residue is taken up in ethyl acetate, and HCl gas is added to the solution. The resulting crystals of the hydrochloride of the (5S,6R)-isomer of the title compound are filtered off and washed with ethyl acetate, melting point 125°–126° C., identical to the product of Example 4. The same product is obtained on isomerisation in toluene (16 hours, 110° C.).

The crude mixture of the (2S,3S)- and (2R,3S)-isomers of 2-benzoylaminomethyl-3-hydroxybutyric acid ethyl ester obtained from the baker's yeast reduction of Example 1 can be cyclised directly with thionyl chloride analogously to Example 4 and isomerised with 1,8-diazabicyclo[5.4.0]-undec-7-ene in toluene at 110° C. for 16 hours. The introduction of HCl gas into the ethyl acetate solution yields the hydrochloride of the (5S,6R)-isomer of the title compound, m.p. 125°–126° C.

EXAMPLE 7

(2S,3R)-2-aminomethyl-3-hydroxybutyric acid 3 g of (5S,6R)-6-methyl-2-phenyl-5,6-dihydro-1,3,4H-oxazinyl-5-carboxylic acid ethyl ester are dissolved in 3 ml of water; 2 ml of 16% hydrochloric acid are added and the whole is heated at reflux for 5 hours. The solution is cooled to 4° C., the crystalline benzoic acid is filtered off and washed with water and the filtrate is completely concentrated by evaporation. The oily residue is stirred with four 20 ml portions of ethyl acetate in order to complete the reaction, and the hydrochloride of the title compound assumes a crystalline form and can be filtered off. M.p. 120°–123° C.; TLC (UPC$_{12}$, water) $R_f$=0.8; $[\alpha]_D$=−11.0° (water, c=0.81%); IR (KBr) 1719, 1623, 1486 cm$^{-1}$.

EXAMPLE 8

(3S,1'R)-3-(1'-hydroxyethyl)-2-azetidinone

A suspension of 266 mg of (2S,3R)-2-aminomethyl-3-hydroxybutyric acid, 600 mg of triphenylphosphine, 50 mg of 2-mercaptopyridine and 200 mg of manganese dioxide in 5 ml of acetonitrile is heated at 70° C. for 6 hours. The reaction mixture is concentrated and chromatographed on silica gel with ethyl acetate. The title compound is recrystallised from tetrahydrofuran. M.p. 101° C.; TLC (silica gel, ethyl acetate) $R_f$=0.15;

$[\alpha]_D = -64.2°$ (DMSO, c=1.18%); IR (CH$_2$Cl$_2$) 3604, 3415, 1758 cm$^{-1}$.

In a larger batch, 15 g of (2S,3R) -2-aminomethyl-3-hydroxybutyric acid hydrochloride is made into a slurry in 50 ml of methylene chloride; 12.5 ml of triethylamine are added and the mixture is stirred at room temperature for 16 hours. The freed amino acid is filtered off and dried. 2.36 g of triphenylphosphine and 1.99 g of 2,2'-dipyridyldisulphide are added to 1.26 g of this amino acid in 10 ml of acetonitrile and the mixture is heated at 80° C. for 2 hours. The reaction mixture is concentrated by evaporation in a rotary evaporator and chromatographed with ethyl acetate on 120 g of silica gel. M.p. 101° C. (from tetrahydrofuran).

EXAMPLE 9

(3R,4R,1'R)-4-acetoxy-3-(1'-hydroxyethyl)-2-azetidinone

A solution of 4 g of (3S,1'R)-3-(1'-hydroxyethyl)-2-azetidinone and 1 g of tetrabutylammonium tetrafluoroborate in 50 ml of glacial acetic acid and 1 ml of water is electrolysed for 4 hours on platinum electrodes in an undivided cell at a current density of 50 mA/cm$^2$. The solvent is removed with toluene in a rotary evaporator and the residue is purified by chromatography on silica gel with ethyl acetate. M.p. 103°–105° C.; $[\alpha]_D = +59.7°$ (chloroform, c=0.36%); UV (chloroform) $\lambda_{max}=269$ nm ($\epsilon=73$); IR (chloroform) 3602, 3406, 1784, 1366 cm$^{-1}$; TLC (silica gel, ethyl acetate) R$_f$0.51.

Instead of in glacial acetic acid, the electrolysis can be carried out in the following mixtures of solvents:

glacial acetic acid/acetonitrile 1:1 and 1:9, glacial acetic acid/acetonitrile/ethyl acetate 1:2:9. Sodium tetrafluoroborate, lithium tetrafluoroborate and ammonium nitrate are also suitable as conducting salts. Platinum (foil, net, wire), VA4 and glass carbon may be used as anodes.

EXAMPLE 10

4(R)-(N-allyloxycarbonylglycylthio)-3(S)-(1'(R)-hydroxyethyl)-2-azetidinone

A solution of 426 mg of the dicyclohexylammonium salt of N-allyloxycarbonyl-thioglycine in 1.2 ml of 1N aqueous sodium hydroxide solution is washed three times with 1.5 ml of CH$_2$Cl$_2$ and adjusted to pH 8–9 with 0.1N hydrochloric acid. The resulting aqueous thiolic acid solution is poured at 25° C. into a solution of 173.2 mg of (3R,4R,1'R)-4-acetoxy-3-(1'-hydroxyethyl)-2-azetidinone in 1.7 ml of acetonitrile. After the addition of 0.1 ml of 0.1N aqueous sodium hydroxide solution, the mixture is stirred for a further 35 minutes at 21°–23° C. For working up, 250 ml of ethyl acetate and 30 g of NaCl are placed in a separating funnel and the reaction mixture is added thereto. After thorough shaking and separation of the aqueous phase, the organic phase is washed once more with 50 ml of 5% aqueous NaHCO$_3$ solution and twice with 50 ml of brine and dried over sodium sulphate. The solvent is removed in a rotary evaporator. The title compound is obtained in the form of an amorphous powder. The crude product can be purified by chromatography on silica gel (toluene/ethyl acetate 2:3). R$_f$ value 0.23 (Merck precoated plates, toluene/ethyl acetate=1:4, ninhydrin as developing reagent).

We claim:

1. A compound of the formula

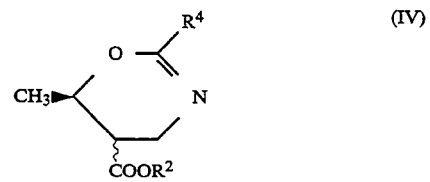

(IV)

in which R$^2$ is an esterifying radical and R$^4$ is selected from the group consisting of lower alkyl, cycloalkyl, aryl, lower alkoxy, aryloxy, and aryl-lower alkoxy, a pure diastereomer thereof or a salt thereof.

2. A compound according to claim 1 of formula IV, in which R$^2$ represents lower alkyl, cycloalkyl, or aryl-lower alkyl, and R$^4$ represents lower alkyl, cyloalkyl, aryl, lower alkoxy, aryloxy, or aryl-lower alkoxy, a pure diastereomer thereof or a salt thereof.

3. A compound according to claim 1 of formula IV, in which R$^2$ represents lower alkyl, and R$^4$ represents lower alkyl or aryl, a pure diastereomer thereof or a salt thereof.

4. (5S,6R)-6-Methyl-2-phenyl-5,6-dihydro-1,3,4H-oxazinyl-5-carboxylic acid ethyl ester according to claim 1.

5. (5R,6R)-6-Methyl-2-phenyl-5,6-dihydro-1,3,4H-oxazinyl-5-carboxylic acid ethyl ester according to claim 1.

6. A compound according to claim 1, wherein R$^2$ is C$_1$–C$_4$alkyl and R$^4$ is C$_1$–C$_4$alkyl or C$_6$C$_{10}$aryl, which may be substituted by methyl, hydroxy, methoxy, acetoxy, chloro, bromo, or nitro, a pure diastereomer thereof or a salt thereof.

7. A compound according to claim 6 of the formula IVa

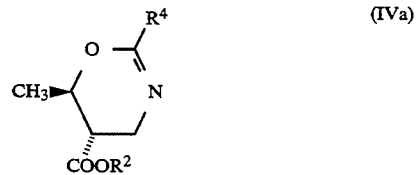

(IVa)

or a salt thereof.

8. 6-Methyl-2-phenyl-5,6-dihydro-1,3,4H-oxazinyl-5-carboxylic acid ethyl ester according to claim 1.

* * * * *